United States Patent
Lee (10) Patent No.: US 11,051,750 B2
(45) Date of Patent: Jul. 6, 2021

(54) NON-CONTACT BLOOD CIRCULATION DETECTION SYSTEM AND METHOD THEREOF

(71) Applicant: Zoetek Inc., New Taipei (TW)

(72) Inventor: Ren-Guey Lee, Taipei (TW)

(73) Assignee: ZOETEK INC., New Taipei (TW)

(*) Notice: Subject to any disclaimer, the term of this patent is extended or adjusted under 35 U.S.C. 154(b) by 100 days.

(21) Appl. No.: 16/552,470

(22) Filed: Aug. 27, 2019

(65) Prior Publication Data

US 2021/0059598 A1 Mar. 4, 2021

(51) Int. Cl.
| | |
|---|---|
| *A61B 5/00* | (2006.01) |
| *A61B 5/01* | (2006.01) |
| *G06T 7/00* | (2017.01) |
| *G01J 5/00* | (2006.01) |

(52) U.S. Cl.
CPC .......... *A61B 5/445* (2013.01); *A61B 5/01* (2013.01); *G06T 7/0012* (2013.01); *A61B 5/0075* (2013.01); *A61B 5/7425* (2013.01); *A61B 2576/02* (2013.01); *G01J 2005/0077* (2013.01); *G06T 2207/30088* (2013.01); *G06T 2207/30096* (2013.01)

(58) Field of Classification Search
CPC ......... A61B 5/445; A61B 5/01; A61B 5/0075; A61B 5/7425; A61B 2576/02; G06T 7/0012; G06T 2207/30088; G06T 2207/30096; G01J 2005/0077
See application file for complete search history.

(56) References Cited

U.S. PATENT DOCUMENTS

| | | | |
|---|---|---|---|
| 10,269,112 B2 | 4/2019 | Spahn et al. | |
| 2008/0188733 A1* | 8/2008 | Al-Ali | A61B 5/6832 600/364 |
| 2017/0024885 A1* | 1/2017 | Miyazaki | A45D 44/00 |
| 2019/0216333 A1* | 7/2019 | Lai | G06F 16/55 |

* cited by examiner

*Primary Examiner* — Brenda C Bernardi
(74) *Attorney, Agent, or Firm* — Muncy, Geissler, Olds & Lowe, P.C.

(57) ABSTRACT

A non-contact blood circulation detection system and method thereof is provided. The non-contact blood circulation detection system comprises a thermal image acquisition module, a non-contact blood oxygen detection device and an information processing module. The thermal image acquisition module faces to a biological skin and generates a thermal image corresponding to the biological skin when being activated; the non-contact blood oxygen detection device faces to a biological skin and generates a blood oxygen image corresponding to the biological skin when being activated, and the information processing module is in information connection with the thermal image acquisition module and the non-contact blood oxygen detection device so as to receive the thermal image and the blood oxygen image, and generates a blood circulation image on the basis of the thermal image and the blood oxygen image, wherein the blood circulation image is a two-dimensional image.

10 Claims, 6 Drawing Sheets

NON-CONTACT BLOOD CIRCULATION DETECTION SYSTEM AND METHOD THEREOF

FIELD OF THE INVENTION

The invention relates to a blood circulation detection system and method thereof, in particular to a blood circulation detection system and method thereof which are implemented in a non-contact manner and with a detection result which is represented by a two-dimensional image.

BACKGROUND OF THE INVENTION

U.S. Pat. No. 10,269,112 discloses a technique for assisting in assessing the extent of damage to a lesion in a biological skin and subcutaneous tissue by gray scale thermal imaging, which may assist medical personnel in assessing the range of the lesion.

However, the deterioration and restoration effect of the lesion is closely related to the blood circulation condition of the surrounding tissues of the lesion, for example, a long-term bedridden patient is liable to have symptoms, such as pressure sores and the like. Medical personnel can only positively treat the position of the pressure sores if a range and a state of the pressure sores are evaluated by thermal imaging only. However, when the position with the pressure sores is still in a low blood circulation state for a long time, the pressure sores from the bedridden patient is unable to be cured, and even the problem of deterioration occurs.

SUMMARY OF THE INVENTION

The main object of the present invention is directed to solve the problem derived from conventional techniques that do not incorporate blood circulation assessment.

To achieve the above object, the present invention provides a non-contact blood circulation detection system comprising a thermal image acquisition module, a non-contact blood oxygen detection device and an information processing module, wherein the thermal image acquisition module faces to a biological skin and generates a thermal image corresponding to the biological skin when being activated, the thermal image is composed of a plurality of first pixels, each of the plurality of first pixels comprises a first color value, and each of the plurality of first pixels comprises a first coordinate in the thermal image. The non-contact blood oxygen detection device comprises an infrared sensing module and a red light sensing module, wherein the non-contact blood oxygen detection device faces to the biological skin and generates a blood oxygen image corresponding to the biological skin when being activated, the blood oxygen image is composed of a plurality of second pixels, each of the plurality of second pixels comprises a second color value, each of the plurality of second pixels comprises a second coordinate in the blood oxygen image, and each of the third coordinate plurality of second coordinates corresponds to one of the plurality of first coordinates. The information processing module is in information connection with the thermal image acquisition module and the non-contact blood oxygen detection device and receives the thermal image and the blood oxygen image to generate a blood circulation image, wherein the blood circulation image is composed of a plurality of third pixels, each of the plurality of third pixels comprises a third coordinate corresponding to one of the plurality of second coordinates, and a third color value mixed by the first color value of the corresponding one of the plurality of first pixels and the second color value of the corresponding one of the plurality of second pixels.

In an embodiment, the non-contact blood circulation detection system further comprises a camera module in information connection with the information processing module, and the camera module faces to the biological skin and generates a surface image when being activated, and the information processing module receives the surface image to superimpose the blood circulation image on the surface image.

In an embodiment, the surface image is a gray scale image, and a plurality of first color values and a plurality of second color values are in a same color system.

In an embodiment, the surface image is processed by the information processing module to be a gray scale image, and a plurality of first color values and a plurality of second color values are in a same color system.

In an embodiment, a plurality of first color values and a plurality of second color values are in a same color system.

Besides, the invention also provides a non-contact blood circulation detection method, which comprises the following steps:

step one: detecting a biological skin by a thermal image acquisition module to obtain a thermal image, and detecting the biological skin by a non-contact blood oxygen detection device to obtain a blood oxygen image, wherein the thermal image is composed of a plurality of first pixels, each of the plurality of first pixels comprises the first color value, and each of the plurality of first pixels comprises a first coordinate in the thermal image; the blood oxygen image is composed of a plurality of second pixels, each of the plurality of second pixels comprises a second color value, each of the plurality of second pixels comprises a second coordinate in the blood oxygen image, and each of the plurality of second coordinates corresponds to one of the plurality of first coordinates; and step two: receiving the thermal image and the blood oxygen image by an information processing module, mixing each of the first color value of the plurality of first pixels with the second color value of one of the plurality of second pixels on a basis of corresponding relations formed between the plurality of second coordinates and one of the plurality of first coordinates respectively to generate a third pixel displayed by a third color value, wherein a plurality of third pixels compose of a blood circulation image, and the blood circulation image is a two-dimensional image.

In an embodiment, the step one further comprises a first substep of photographing a biological skin by using a camera module to obtain a surface image. The step two further comprises a second substep of superimposing the surface image on the blood circulation image by the information processing module.

In an embodiment, the surface image is a gray scale image, and the plurality of first color values and the plurality of second color values are in a same color system.

In an embodiment, the surface image is processed by the information processing module to be a gray scale image, and the plurality of first color values and the plurality of second color values are in a same color system.

In an embodiment, the plurality of first color values and the plurality of second color values are in a same color system.

By the implementation of the present invention, compared with the conventional application, the present invention has the following characteristics: the blood circulation image is formed by the thermal image and the blood oxygen image, so that medical personnel can clearly know and evaluate the current state of the biological skin and subcutaneous tissue by the blood circulation image so as to make a more appropriate treatment.

DETAILED DESCRIPTION OF THE PREFERRED EMBODIMENTS

The detailed description and technical contents of the present invention will now be described with reference to the drawings as follows.

Figure 1:
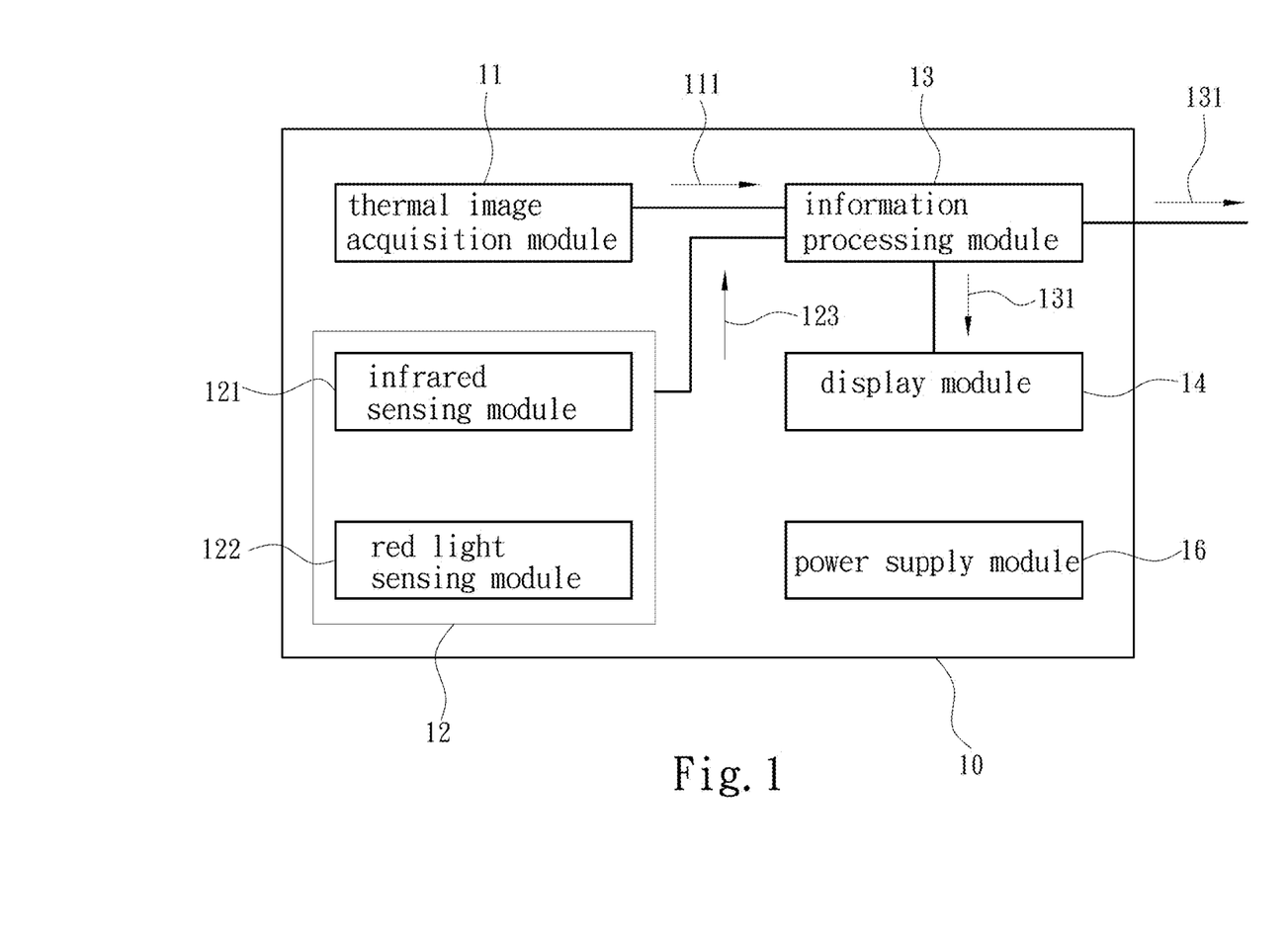
FIG. 1 is a schematic diagram showing the composition of a unit according to an embodiment of the present invention.
Figure 2:
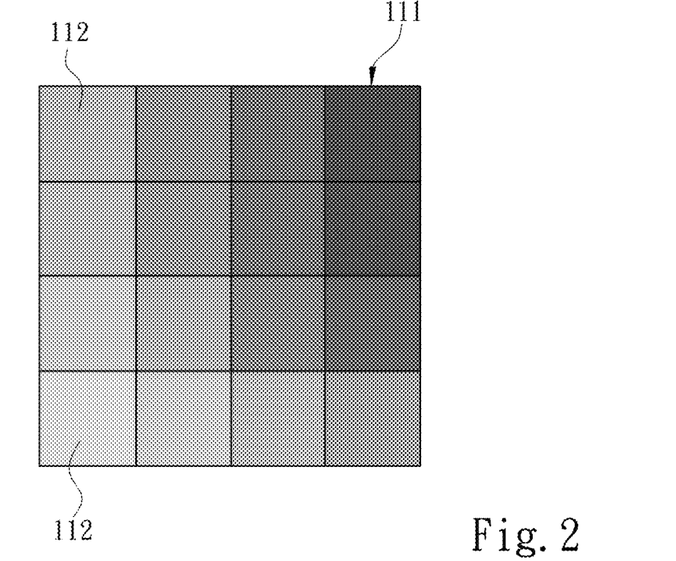
FIG. 2 is a thermal image schematic diagram of an embodiment of the present invention.

Referring to FIG. 1, the present invention provides a non-contact blood circulation detection system 10 for detecting a biological skin to learn a blood circulation status of a subcutaneous tissue of the biological skin. The non-contact blood circulation detection system 10 includes a thermal image acquisition module 11, a non-contact blood oxygen detection device 12 and an information processing module 13 which is in information connection with the thermal image acquisition module 11 and the non-contact blood oxygen detection device 12, wherein the thermal image acquisition module 11, the non-contact blood oxygen detection device 12 and the information processing module 13 is able to be arranged in a same shell. Referring to FIG. 2, the thermal image acquisition module 11 faces to the biological skin and generate a thermal image 111 corresponding to the biological skin when being activated, the thermal image 111 is composed of a plurality of first pixels 112, each of the plurality of first pixels 112 comprises a first color value, and each of the plurality of first pixels 112 comprises a first coordinate in the thermal image 111. By way of example, as depicted in FIG. 2, each of the plurality of first pixels 112 respectively displays a temperature at a position or a point of the biological skin, and the first color value is determined by the temperature level, as the temperature is increased, a color of the first color value is closer to a dark color. On the contrary, as the temperature is decreased, the color of the first color value is closer to a light color. Thus, the color of each of the plurality of first pixels 112 may not be the same. In addition, a variation in the first color value may be in a same color system, or in a different color system. For example, when the temperature is high, the first color value is in a warm color system, and when the temperature is low, the first color value is in a cold color system, wherein the warm color system may be red, orange, etc., and the cold color system may be blue, etc. Furthermore, the plurality of first pixels 112 are sequentially arranged on a basis of the image size of the thermal image 111, and the first coordinate of each of the plurality of first pixels 112 indicate a position of the first pixel 112 in the thermal image 111. For example, the first coordinate of the plurality of first pixels 112 in the upper left corner of FIG. 2 may be (1, 1), and the first coordinate of the plurality of first pixels 112 in the lower left corner of FIG. 2 may be (1, 4).

Figure 3:
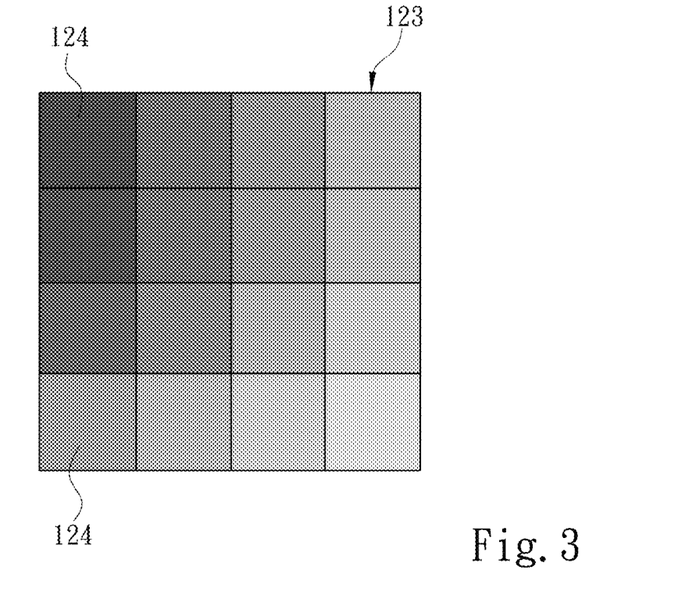
FIG. 3 is a schematic diagram of a blood oxygen image according to an embodiment of the present invention.

Referring to FIGS. 1 and 3, the non-contact blood oxygen detection device 12 of the present invention includes an infrared sensing module 121 and a red light sensing module 122. In an embodiment, the infrared sensing module 121 is implemented for detection with a light source of 940 nm wavelength, while the red light sensing module 122 is implemented for detection with another light source of 660 nm wavelength, and the non-contact blood oxygen detection device 12 faces to the biological skin and generate a blood oxygen image 123 corresponding to the biological skin when being activated. Furthermore, in the implementation process of the non-contact blood oxygen detection device 12, the infrared sensing module 121 and the red light sensing module 122 proceed with detecting of oxyhemoglobin (HbO2) and hemoglobin (Hb) at each position of the biological skin which faces to the non-contact blood oxygen detection device 12, and the non-contact blood oxygen detection device 12 converts to obtain the saturation of peripheral oxygen at each position of the biological skin on the basis of the variation of R value in the detection result, and composes of a blood oxygen image 123 corresponding to the biological skin. The blood oxygen image 123 is composed of a plurality of second pixels 124, the plurality of second pixels 124 respectively comprises a second color value, and each of the plurality of second pixels 124 comprises a second coordinate in the blood oxygen image 123. Continuing with the illustration depicted in FIG. 3, each of the plurality of second pixels 124 respectively displays a saturation of peripheral oxygen (SpO2) of a blood vessel at a position or a point of the biological skin, and the second color value is determined by the saturation of peripheral oxygen. More specifically, as saturation of peripheral oxygen is increased, the color of the second color value is closer to a dark color. On the contrary, as saturation of peripheral oxygen is decreased, the color of the second color value is closer to a light color. In addition, the variation of the second color value may be in the same color system, or in a different color system. For example, the second color value is in a warm color system as the saturation of peripheral oxygen is high enough, and the second color value is in a cold color system as the saturation of peripheral oxygen is low enough. On the other hand, the plurality of second pixels 124 are sequentially arranged on the basis of the image size of the blood oxygen image 123, and the second coordinate of each of the plurality of second pixels 124 indicate a position of the second pixel 124 in the blood oxygen image 123. Further, the second coordinate of the plurality of second pixels 124 in the upper left corner of FIG. 3 may be (1, 1), and the second coordinate of the plurality of second pixels 124 in the lower left corner of FIG. 3 may be (1, 4). Thus, it can be seen that each of the plurality of second coordinates corresponds to one of the plurality of first coordinates in the present invention.

Figure 4:
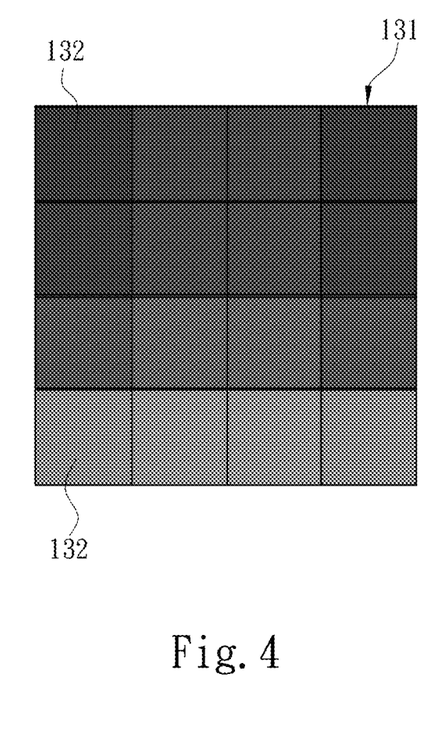
FIG. 4 is a schematic diagram of a blood circulation image according to an embodiment of the present invention.

Referring again to FIGS. 1 and 4, the information processing module 13 is implemented by a computation chip in conjunction with a plurality of electronic components. The information processing module 13 includes the capability of information computing and processing by writing methods, such as programming or the like. Further, the information processing module 13 may receive the thermal image 111 and the blood oxygen image 123 by an information transmission line to generate a blood circulation image 131, and the information processing module 13 may provide the blood circulation image 131 to an external device by a wired or wireless mode. In addition, the information processing module 13 is able to provide the blood circulation image 131 to a display module 14 which belongs to the non-contact blood circulation detection system 10 by another information transmission line, so that the blood circulation image 131 is displayed by the display module 14. Accordingly, the blood circulation image 131 is a two-dimensional image in the present invention, that is, the blood circulation image 131 is a planar image. Additionally, the blood circulation image 131 is composed of a plurality of third pixels 132, each of the plurality of third pixels 132 comprises a third coordinate and a third color value, wherein each of the plurality of third coordinates corresponds to one of the plurality of second coordinates, that is, each of the plurality of third coordinates corresponds to one of the plurality of first coordinates and one of the plurality of second coordinates. On the other hand, the third color value of each of the plurality of third pixels 132 is mixed by the first color value of the corresponding one of the plurality of first pixels 112 and the second color value of the corresponding one of the plurality of second pixels 124. Further, the mixing herein refers to totaling the first color value and the second color value. Accordingly, a better blood circulation is shown as the color of the third color value is deeper. On the contrary, a poorer blood circulation is shown as the color of the third color value is lighter.

Figure 5:
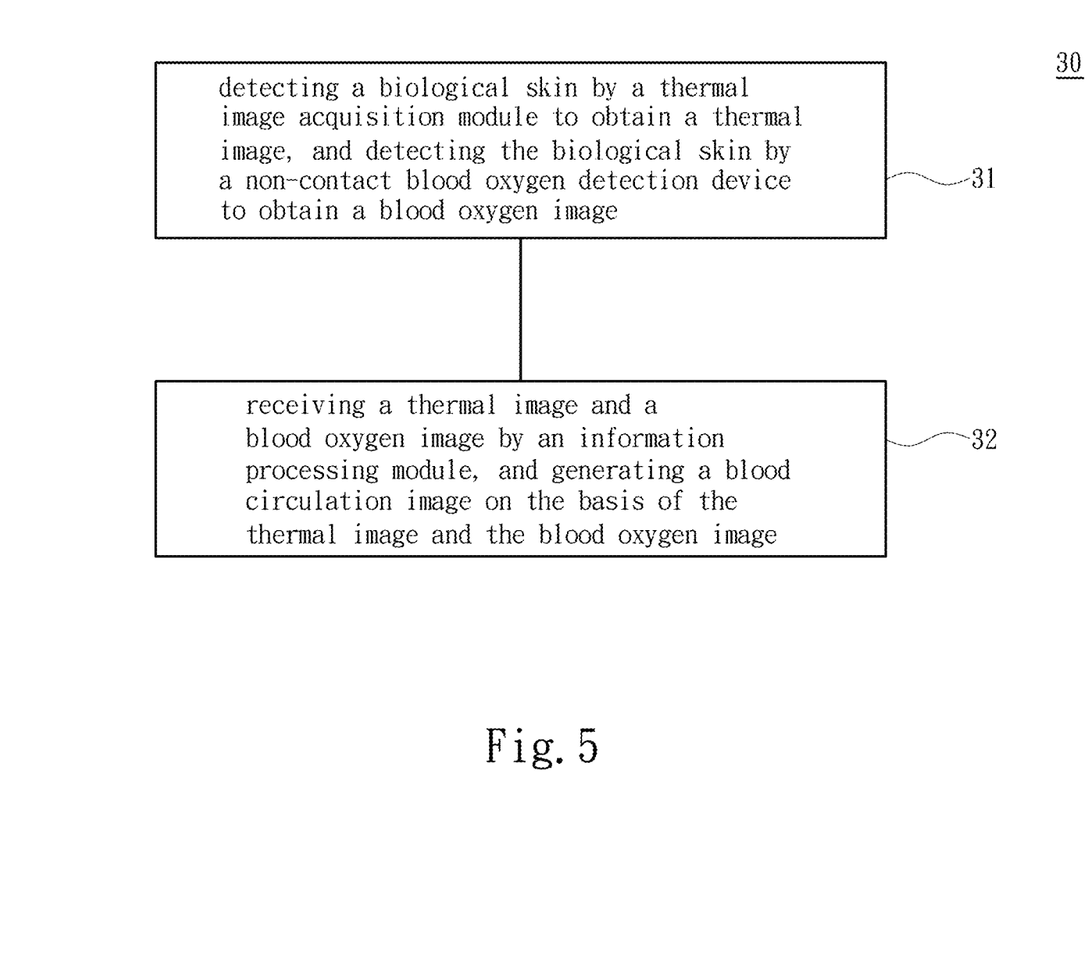
FIG. 5 is a flowchart of a method according to an embodiment of the present invention.

As mentioned above and with reference to FIG. 5, the present invention further provides a non-contact blood circulation detection method 30, including the following steps:

step one 31: respectively detecting the biological skin by the thermal image acquisition module 11 and the non-contact blood oxygen detection device 12 to obtain a thermal image 111 and a blood oxygen image 123, the thermal image 111 is composed of a plurality of first pixels 112, the plurality of first pixels 112 respectively comprise a first color value, and each of the plurality of first pixels 112 comprises a first coordinate in the thermal image 111; the blood oxygen image 123 is composed of a plurality of second pixels 124, the plurality of second pixels 124 respectively comprise a second color value, each of the plurality of second pixels 124 comprises a second coordinate in the blood oxygen image 123, and each of the plurality of second coordinates corresponds to one of the plurality of first coordinates; and step two 32: receiving the thermal image 111 and the blood oxygen image 123 by an information processing module 13, mixing the first color value of each of the plurality of first pixels 112 with the second color value of one of the plurality of second pixels 124 on a basis of corresponding relations formed between the plurality of second coordinates and one of the plurality of first coordinates respectively to generate a third pixel 132 displayed with the third color value, wherein the plurality of third pixels 132 compose of a blood circulation image 131, and the blood circulation image 131 is the two-dimensional image.

Further illustrating the implementation of the foregoing method, in step one 31, the non-contact blood circulation detection system 10 is first applied to a biological skin to be detected, wherein the biological skin corresponding to the non-contact blood circulation detection system 10 may include a lesion. Then, the thermal image acquisition module 11 and the non-contact blood oxygen detection device 12 respectively proceed with detecting of detecting the biological skin to obtain the thermal image 111 and the blood oxygen image 123, and then performing the step two 32.

When the step two 32 is performed, the thermal image 111 and the blood oxygen image 123 are received by the information processing module 13, and the information processing module 13 mixes the first color value of each of the plurality of first pixels 112 with the second color value of one of the plurality of second pixels 124 on the basis of corresponding relations formed between the plurality of second coordinates and one of the plurality of first coordinates respectively, and generates the third pixel 132 displayed with the third color value. By way of further illustration, a second coordinate of one of the plurality of second pixels 124 is (1, 4), and the information processing module 13 then mixes the second pixel 124 with one of the plurality of first pixels 112 with a first coordinate of (1, 4) to produce one of the plurality of third pixels 132. Accordingly, the information processing module 13 generates the blood circulation image 131 after mixing all the plurality of first pixels 112 and the plurality of second pixels 124. In an embodiment, the first color values and the second color values are in the same color system. Accordingly, the blood circulation image 131 will be presented with a monochrome system figure including a shade variation.

Figure 6:
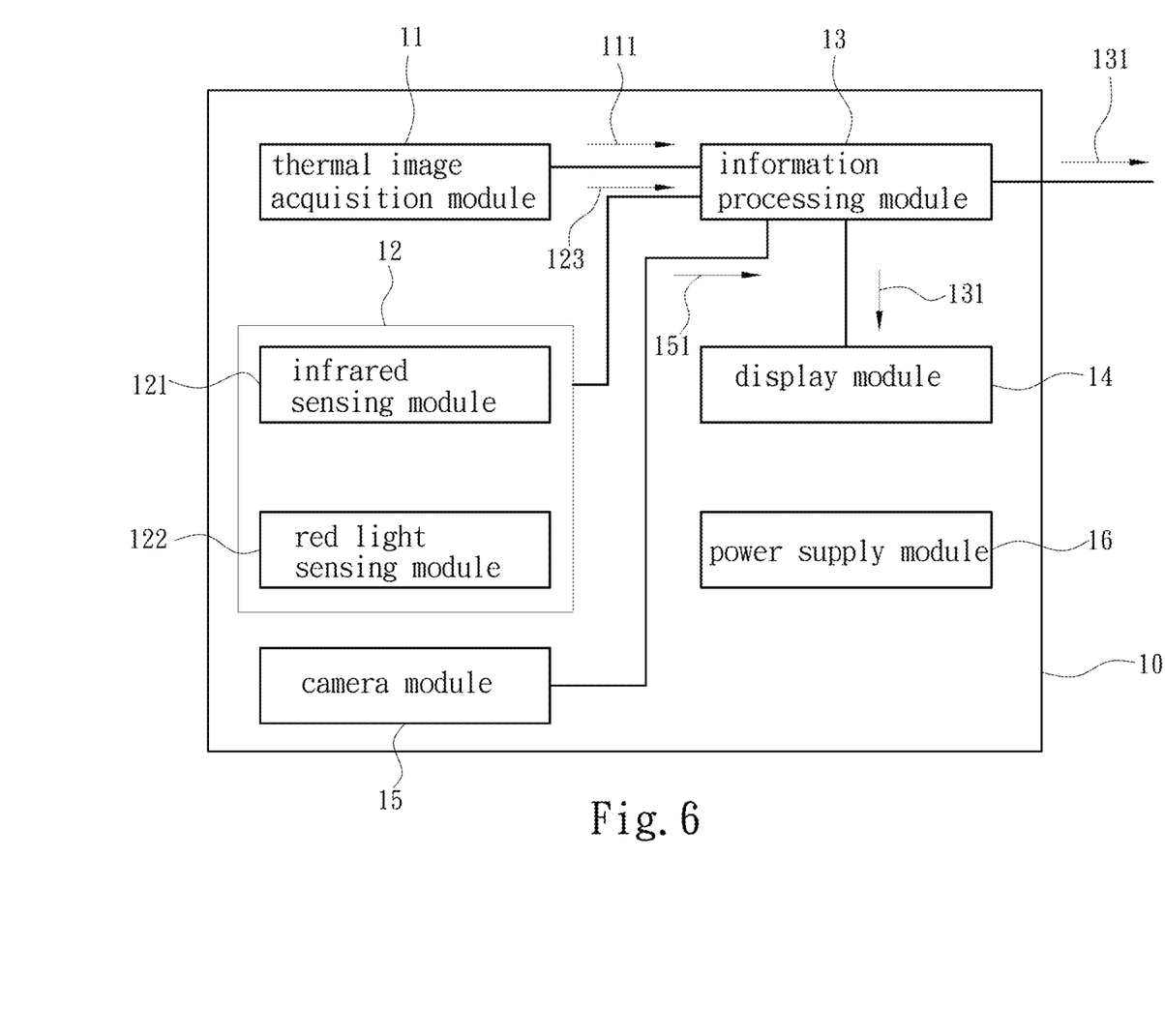
FIG. 6 is a schematic diagram showing the composition of a unit according to another embodiment of the present invention.
Figure 7:
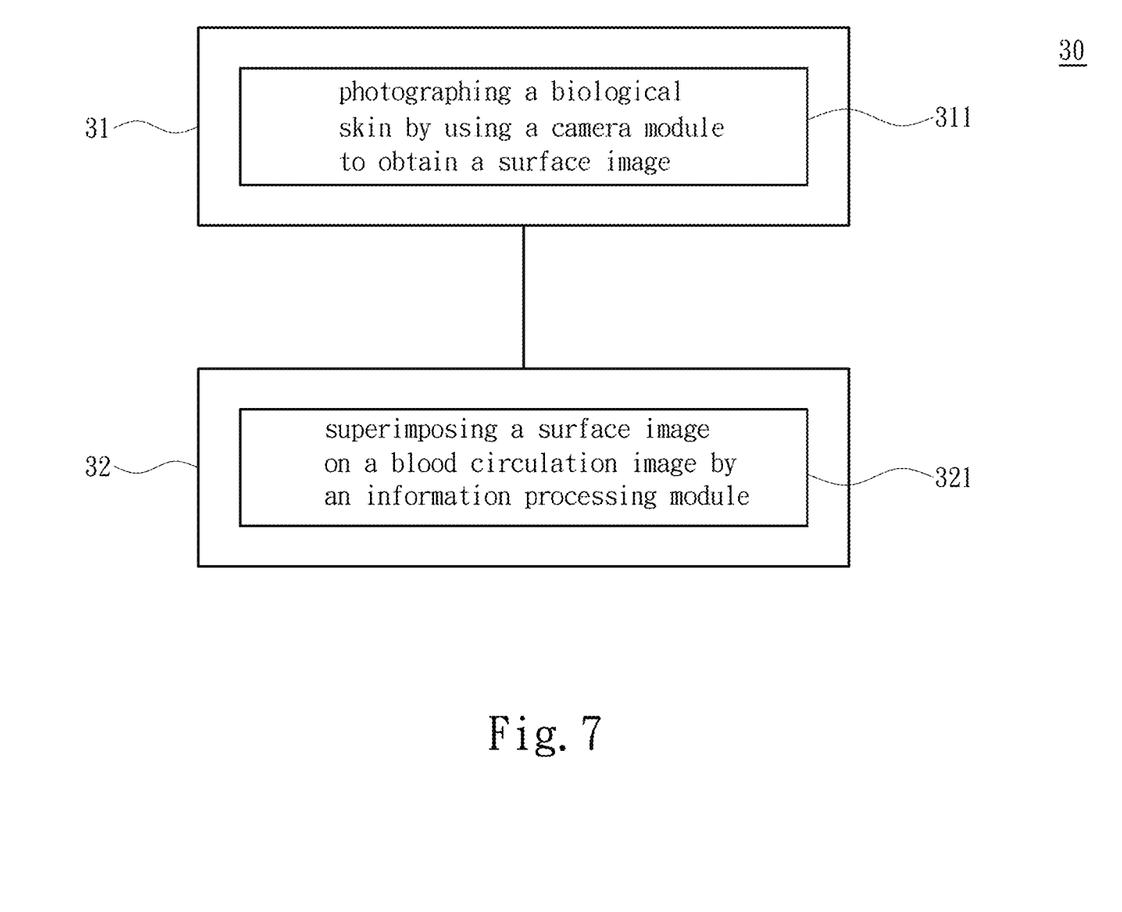
FIG. 7 is a flowchart of a method according to another embodiment of the present invention.

Referring to FIG. 6, in an embodiment, the non-contact blood circulation detection system 10 further includes a camera module 15 in information communication with the information processing module 13; the camera module 15 faces to a biological skin and generate a surface image 151 when being activated, and the information processing module 13 receives the surface image 151 to superimpose the blood circulation image 131 on the surface image 151. Accordingly, referring to FIG. 7, in this embodiment, the step one 31 of the non-contact blood circulation detection method 30 further includes a first substep 311 of photographing the biological skin by using a camera module 15 to obtain the surface image 151. On the other hand, the step two 32 includes a second substep 321 of superimposing the surface image 151 on the blood circulation image 131 by the information processing module 13. Therefore, the position represented by each part of the blood circulation image 131, is able to be more clearly distinguished by superimposing the surface image 151 on the blood circulation image 131. In an embodiment, the surface image 151 is a gray scale image when produced by the camera module 15, and the first color values and the second color values are in the same color system. In another embodiment, the surface image 151 is processed by the information processing module 13 to be a gray scale image, and the first color values and the second color values are also in the same color system. Thereby, the color development effect on the blood circulation image 131 is reduced by the surface image 151 which is gray-scale. In addition, the blood circulation image 131 is able to be subjected to subsequent image processing to make the color development more obvious.

Referring again to FIGS. 1 and 6, in an embodiment, the non-contact blood circulation detection system 10 further includes a power supply module 16, and the power supply module 16 supplies power to portions of the non-contact blood circulation detection system 10 that require power, such as the thermal image acquisition module 11 and the non-contact blood oxygen detection device 12. In addition, the power supply module 16 is able to obtain power by a rechargeable battery, a dry battery or an external power grid.

As described above, in the present invention, the blood circulation image 131 is composed of the thermal image 111 and the blood oxygen image 123, so that medical personnel can clearly understand and evaluate the current state of the biological skin and its subcutaneous tissue by the blood circulation image 131 so as to make a more appropriate treatment.

What is claimed is:

1. A non-contact blood circulation detection system, comprising:
    a thermal imager, the thermal imager facing to a biological skin and generating a thermal image corresponding to the biological skin when being activated, the thermal image being composed of a plurality of first pixels, each of the plurality of first pixels comprising a first color value, and each of the plurality of first pixels comprising a first coordinate in the thermal image;
    a non-contact blood oxygen detection device, comprising an infrared sensor and a red light sensor, wherein the non-contact blood oxygen detection device faces to the biological skin and generates a blood oxygen image corresponding to the biological skin when being activated, the blood oxygen image is composed of a plurality of second pixels, each of the plurality of second pixels comprises a second color value, each of the plurality of second pixels comprises a second coordinate in the blood oxygen image, and each of a plurality of second coordinates corresponds to one of the plurality of first coordinates; and
    an information processor, which is in information connection with the thermal imager and the non-contact blood oxygen detection device and receives the thermal image and the blood oxygen image to generate a blood circulation image, wherein the blood circulation image is a two-dimensional image and is composed of a plurality of third pixels, and each of the plurality of third pixels comprising a third coordinate corresponding to one of the plurality of second coordinates, and a third color value mixed by the first color value of the corresponding one of the plurality of first pixels and the second color value of the corresponding one of the plurality of second pixels.

2. The non-contact blood circulation detection system of claim 1, wherein the non-contact blood circulation detection system further comprises a camera module in information connection with the information processor, the camera module faces to the biological skin and generates a surface image when being activated, and the information processor receives the surface image to superimpose the blood circulation image on the surface image.

3. The non-contact blood circulation detection system of claim 2, wherein the surface image is a gray scale image, and a plurality of first color values and a plurality of second color values are in a same color system.

4. The non-contact blood circulation detection system of claim 2, wherein the surface image is processed by the information processor to be a gray scale image, and a plurality of first color values and a plurality of second color values are in a same color system.

5. The non-contact blood circulation detection system of claim 1, wherein a plurality of first color values and a plurality of second color values are in a same color system.

6. A non-contact blood circulation detection method, comprising the following steps:
    step one: detecting a biological skin by a thermal imager to obtain a thermal image, and detecting the biological skin by a non-contact blood oxygen detection device to obtain a blood oxygen image, wherein the thermal image is composed of a plurality of first pixels, each of the plurality of first pixels comprises a first color value, and each of the plurality of first pixels comprises a first coordinate in the thermal image, the blood oxygen image is composed of a plurality of second pixels, each of the plurality of second pixels comprises a second color value, each of the plurality of second pixels comprises a second coordinate in the blood oxygen image, and each of a plurality of second coordinates corresponds to one of a plurality of first coordinates; and
    step two: receiving the thermal image and the blood oxygen image by an information processor, mixing each of the first color value of the plurality of first pixels with one of the second color value of the plurality of second pixels on a basis of corresponding relations formed between the plurality of second coordinates and one of the plurality of first coordinates respectively to generate a third pixel displayed by a third color value, wherein a plurality of third pixels compose of a blood circulation image, and the blood circulation image is a two-dimensional image.

7. The non-contact blood circulation detection method of claim 6, wherein the step one further comprises a first substep of photographing the biological skin by using a camera module to obtain a surface image; the step two further comprises a second substep of superimposing the surface image on the blood circulation image by the information processor.

8. The non-contact blood circulation detection method of claim 7, wherein the surface image is a gray scale image, and a plurality of first color values and a plurality of second color values are in a same color system.

9. The non-contact blood circulation detection method of claim 7, wherein the surface image is processed by the information processor to be a gray scale image, and a plurality of first color values and a plurality of second color values are in a same color system.

10. The non-contact blood circulation detection method of claim 6, wherein a plurality of first color values and a plurality of second color values are in a same color system.

* * * * *